(12) United States Patent
Richter et al.

(10) Patent No.: US 10,792,430 B2
(45) Date of Patent: Oct. 6, 2020

(54) FREE-JET DOSING SYSTEM FOR APPLYING A FLUID INTO OR UNDER THE SKIN

(71) Applicant: Fraunhofer-Gesellschaft zur Foerderung der angewandten Forschung e.V., Munich (DE)

(72) Inventors: Martin Richter, Munich (DE); Martin Wackerle, Assling (DE); Christian Wald, Munich (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 805 days.

(21) Appl. No.: 15/373,222

(22) Filed: Dec. 8, 2016

(65) Prior Publication Data
US 2017/0157329 A1    Jun. 8, 2017

(30) Foreign Application Priority Data

Dec. 8, 2015   (DE) ........................ 10 2015 224 624

(51) Int. Cl.
*A61M 5/30*    (2006.01)
*A61K 9/00*    (2006.01)
(Continued)

(52) U.S. Cl.
CPC ......... *A61M 5/3007* (2013.01); *A61K 9/0019* (2013.01); *A61K 9/0021* (2013.01);
(Continued)

(58) Field of Classification Search
CPC .... A61M 5/30; A61M 5/3007; A61M 5/3015; A61M 5/2053; A61M 5/2046;
(Continued)

(56) References Cited

U.S. PATENT DOCUMENTS 6,589,229 B1 *  7/2003  Connelly .......... A61M 5/14248
                                                604/890.1
7,070,577 B1 *  7/2006  Haller ............... A61M 5/14276
                                                604/131

(Continued)

FOREIGN PATENT DOCUMENTS

JP    2002126092 A    5/2002
JP    2006524120 A    10/2006
(Continued)

OTHER PUBLICATIONS

"Injex Pharma Group", "Injex Pharma Group Injections Without Needle" [online], [retrieved on Jun. 30, 2017], [Retrieved from <http://www.injex.de/>], Feb. 18, 2016, 1-2.
(Continued)

*Primary Examiner* — Tiffany Legette
*Assistant Examiner* — Tiffany Legette-Thompson
(74) *Attorney, Agent, or Firm* — Perkins Coie LLP; Michael A. Glenn

(57) ABSTRACT

A free-jet dosing system for administering a fluid into or under the skin having a micropump and a nozzle arranged on the outlet side. The micropump has an inlet and an outlet and is configured to transport a fluid from the inlet to the outlet and to generate a blocking pressure of at least 20 bar at the outlet. The nozzle is configured to output the fluid output at the outlet as a free jet at a fluid pressure so that the fluid of the free jet may be injected into the skin.

15 Claims, 6 Drawing Sheets

(51) Int. Cl.
*A61M 5/20* (2006.01)
*A61M 39/24* (2006.01)
*A61M 5/42* (2006.01)
*A61M 5/48* (2006.01)

(52) U.S. Cl.
CPC .......... *A61K 9/0097* (2013.01); *A61M 5/2053* (2013.01); *A61M 5/30* (2013.01); *A61M 39/24* (2013.01); *A61M 5/422* (2013.01); *A61M 5/48* (2013.01); *A61M 5/484* (2013.01); *A61M 5/488* (2013.01); *A61M 2205/0205* (2013.01); *A61M 2205/3331* (2013.01); *A61M 2209/088* (2013.01)

(58) Field of Classification Search
CPC ...... A61M 5/14248; A61M 2005/3022; A61M 2005/3128; A61M 5/48; A61M 5/484; A61M 5/488; A61M 2209/088; A61M 2205/3331; A61M 2205/0205; A61M 39/24; A61K 9/0019; A61K 9/0097; A61K 9/0021; A61K 9/0098
See application file for complete search history.

(56) References Cited

U.S. PATENT DOCUMENTS

| | | | |
|---|---|---|---|
| 2009/0131860 A1* | 5/2009 | Nielsen | A61M 5/14248 604/66 |
| 2010/0179473 A1 | 7/2010 | Genosar | |
| 2010/0263757 A1* | 10/2010 | Fernandes | B01L 3/502707 137/832 |
| 2010/0327699 A1* | 12/2010 | Hassanali | C04B 41/009 310/340 |
| 2011/0061526 A1 | 3/2011 | Wackerle et al. | |
| 2013/0183209 A1* | 7/2013 | Richter | A61M 5/16877 422/403 |
| 2014/0257186 A1* | 9/2014 | Kerr | A61L 29/085 604/164.1 |
| 2015/0157809 A1* | 6/2015 | Park | A61M 5/204 604/131 |

FOREIGN PATENT DOCUMENTS

| | | |
|---|---|---|
| JP | 2012506279 A | 3/2012 |
| WO | 2009136304 A2 | 11/2009 |

OTHER PUBLICATIONS

Hemond, Brian D. et al., "A Lorentz-Forced Actuated Autoloading Needle-Free Injector", Proceedings of the 28th IEEE EMBS Annual International Conference, New York, Aug. 2006, 679-682.

Herz, Markus, "Optimierung Der Foerderrate Einer Piezoelektrischen Hochleistungs-Mikropumpe", Dissertation Technische Universitaet Muenchen, Lehrstuhl Fuer Mikrotechnik und Medizingeraetetechnik, Jun. 22, 2011, 1-124.

Mitragotri, Samir et al., "Recent Developments in Needle-Free Drug Delivery", The Bridge (USPS 551-240) National Academy of Engineering, vol. 38, No. 4, 2008, Cover 1-72.

Mutschler, K. et al., "EndoMediskop Trans-Endoscopic Microinjection for Flexible Endoscopy", Biomed Tech 2012; 57 (Suppl. 1) by Walter de Gruyter, 2012, 361-364.

Richter, M., "Blockierdruck Von Mikropumpen, Beispielsrechnun Fuer Mikropumpen Fuer Jet Injection", Munich, Nov. 4, 2016, 1-2.

Scherbaum, W. A., "Nadelfreie Insulininjektionssysteme-Ein Wesentlicher Fortschritt Bei Der Insulintherapie?", Deutsches Diabetes-Forschungsinstitut Duesseldorf, [online], [retrieved on Jun. 30, 2017], [Retrieved from <http://www.diabetes-deutschland.de/archiv/archiv_2847.htm>, 2008, 1-2.

Wackerle, M. et al., "A Novel Device for High Frequency Ejection of Nanoliter Jets", 8th International Conference on New Actuators, Jun. 2002, 227-230.

Weinzierl, Susanne, "Konzept Zur Branchenanalyse Zur Kommerzialisierung Einer Piezoelektrisch Angetriebenen Mikropumpe Fuer Das Indikationsgebiet Diabetes Mellitus", Masterarbeit, Georg Siemon-Ohm Hochschule Nuernberg, Fakultaet Fuer Betriebswirtschaft, realized for Fraunhofer EMFT, Aug. 31, 2013, 1-128.

* cited by examiner

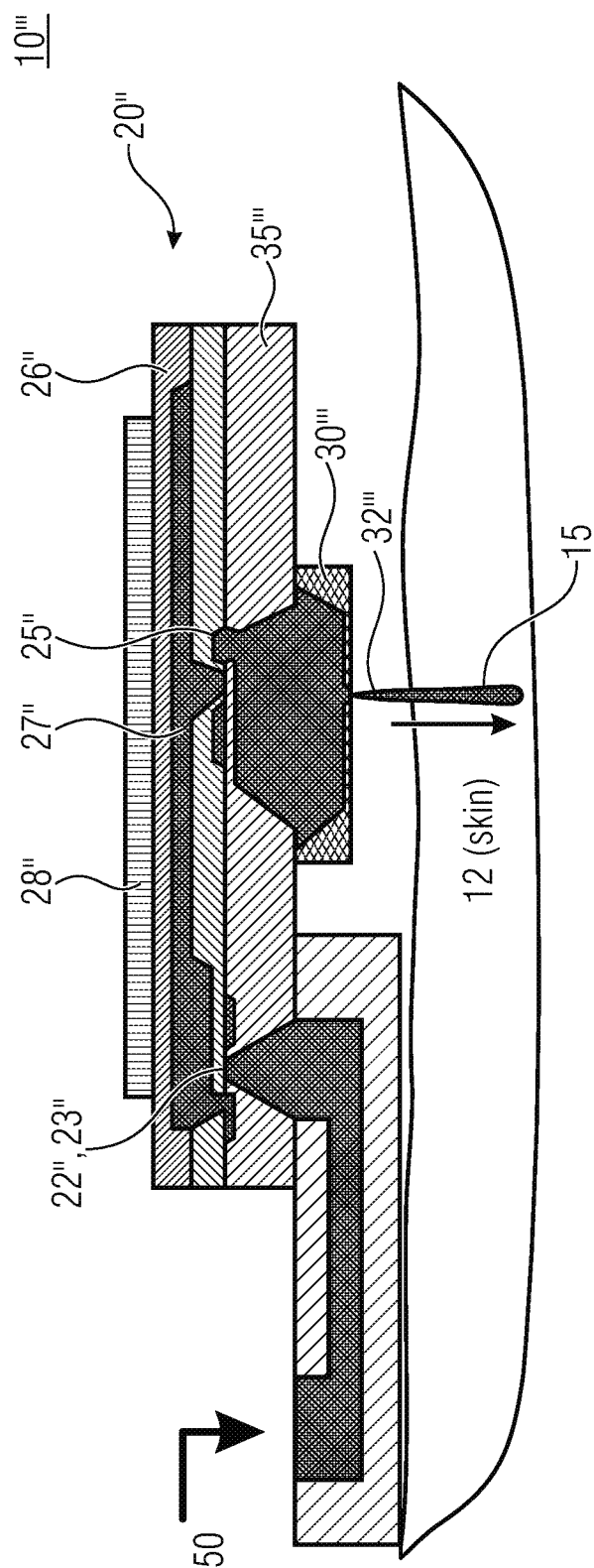

Design example for varying chip sizes of micropumps

| jet injection design example | | | | |
|---|---|---|---|---|
| design | 7x7mm2 | 5x5mm2 | 3.5x3.5mm2 | 2.5x2.5mm2 |
| ΔV [nl] design | 61 | 22 | 9 | 3 |
| Cp [nl/kPa] design | 0.0181 | 0.0047 | 0.0022 | 0.0010 |
| pblock [kPa] | 3390 | 4556 | 4164 | 3620 |
| Theory of actuator | | | | |
| E mod. membr. (silicon) [Pa] | 1.60E+11 | 1.60E+11 | 1.60E+11 | 1.60E+11 |
| E modulus piezo [Pa] | 8.00E+10 | 8.00E+10 | 8.00E+10 | 8.00E+10 |
| thickness membrane [m] | 2.00E-04 | 1.50E-04 | 1.00E-04 | 8.00E-05 |
| thickness piezo [m] | 4.00E-04 | 3.50E-04 | 2.50E-04 | 1.60E-04 |
| radius membrane [m] | 3.10E-03 | 2.25E-03 | 1.65E-03 | 1.20E-03 |
| radius piezo [m] | 2.79E-03 | 2.03E-03 | 1.49E-03 | 1.08E-03 |
| d31 coeff [m/V] | 2.50E-10 | 2.50E-10 | 2.50E-10 | 2.50E-10 |
| poisson number [1] | 2.50E-01 | 2.50E-01 | 2.50E-01 | 2.50E-01 |
| e-field positive [V/m] | 1.50E+06 | 1.50E+06 | 1.50E+06 | 1.50E+06 |
| e-field negative [V/m] | -4.00E+05 | -4.00E+05 | -4.00E+05 | -4.00E+05 |
| positive voltage [V] | 600 | 525 | 375 | 240 |
| negative voltage [V] | -160 | -140 | -100 | -64 |
| voltage stroke [V] | 760 | 665 | 475 | 304 |
| CP | 1.812E-17 | 4.747E-18 | 2.186E-18 | 9.524E-19 |
| CE* | -8.E-14 | -3.E-14 | -2.E-14 | -1.E-14 |

Remark: smaller chip sizes are better for jet injection (as to lower voltages)

Fig. 5b

FREE-JET DOSING SYSTEM FOR APPLYING A FLUID INTO OR UNDER THE SKIN

CROSS-REFERENCE TO RELATED APPLICATION

This application claims priority from German Application No. 10 2015 224 624.8, which was filed on Dec. 8, 2015, and is incorporated herein by reference in its entirety.

BACKGROUND OF THE INVENTION

Embodiments of the present invention relate to a free-jet dosing system for applying a fluid into or under the skin. Further embodiments relate to a wearable arm strap comprising a corresponding dosing system, and to a patch comprising such a dosing system.

Subcutaneous application relates to applying a substance under the skin, i.e., for example, into connective tissue or fatty tissue, in the first place. Applying a substance into muscular tissue or the blood stream is also covered by this general definition.

Administering a drug or medication may be done in various ways. Orally taking pills or liquids is most widespread, but anally applied suppositories, inhalation over the lungs, eye drops, applying ointments to the skin, systemic administration by means of intravenous infusions, subcutaneous application by means of syringes or implantable medication dosing systems are further examples. Macromolecules, like peptides or proteins, cannot be administered through pills, but by means of injections [1].

Administering insulin is an example thereof. At present, the subcutaneous application of insulin entails being pricked by a needle, and pain. Diabetes is spreading quickly, in particular in states like China, India or Brazil, caused by changing eating habits, but also in developed countries, above all caused by the demographic change. In accordance with current market analysis, the market for "insulin delivery devices" (without insulin) is increasing from 8.78 billion U.S. Dollars at present to 13.8 billion U.S. Dollars in 2019 [7]. Especially in the therapy of diabetes, administering insulin by means of inhalation or orally (by encapsulation) has been researched over the past few years, however these methods have not gained acceptance on the market. The cause here is, above all, the inadequate dosing precision (or bio-availability) of the alternative methods, only with subcutaneous (or also intravenous) injections can the quantity of insulin reaching the blood stream be defined precisely. However, injections entail pain and necessitate the patient to actively contribute to administering the insulin.

So-called "pens" are widespread at present: a preset quantity of insulin is automatically injected to the patient via a needle, by spring latching. However, this necessitates pricking by a needle several times a day, entailing pain. "Patch pumps" (supplier: Omnipod) which are worn at the body are a new trend, they only necessitate pricking every three days. However, after three days, the catheter comprising the patch pump has to be exchanged in order to avoid infections. At present, there is no low-pain and needleless technology for subcutaneously applying medication, which would be of high benefit for patients.

Needleless injections have been known since World War II. So-called vaccination guns, which are employed above all in veterinary medicine, have been known, which are, however, not used anymore in humans for problems of sterility. The active substance here is accelerated through an opening by means of a gas or spring at high pressure and shot into the skin. There are improved and approved needleless injection systems, like the system by Injex [3], which apart from diabetes therapy, is also applied for local anesthetics (for example in dental surgery).

However, freedom from pain is not always guaranteed, additionally these are more difficult to handle than pens [4]. Of further disadvantage when compared to the pen is the fact that these are more expensive to purchase and are only paid for by health insurance companies in exceptional circumstances (for example syringe phobia). Additionally, the penetration depths of the medication (which is in the range of several millimeters) cannot be adjusted precisely using these systems, which is, among others, the cause for incomplete freedom from pain.

Over the last few years, various groups of researches have tried to improve needleless injection by new actuator principles: the University of California, Santa Barbara, has performed examinations in order to achieve the high pressure in a better defined manner using piezo stack actuators (instead of spring or gas drive) [1]. As an alternative, the Mass. Institute of Technology (MIT) has developed an injector which uses a piston accelerated using a Lorentz force drive for generating high pressure [5]. The HSG IMIT has examined an injector for usage in an endoscope using the same principle [2]. All these new needleless injectors are able to precisely adjust the pressure profile and, thus, the penetration depth of the medication in principle, injection takes place nearly with no pain, the patient can hardly feel the jet, which is a considerable improvement.

However, a disadvantage of these systems is too small an emission frequency of the micro drops (of a quantity of a few 10 nanoliters). This is caused by the fact that the dosing chamber cannot be filled again sufficiently quickly. The dosing quantities here are limited to about 0.5 to 1.0 µl/s. Additionally, it is very difficult in these systems to reduce the dead volume and, thus, the fluidic capacitances between actuator and nozzle so that the pressure profile cannot be realized in the jet when there are air bubbles. Furthermore, reference is made to WO 2009/136304 which shows a micropump for medical purposes.

Finally, all these systems are very large and expensive in manufacturing so that they are not suitable for integrated application. Therefore, there is need for an improved approach.

SUMMARY

According to an embodiment, a free-jet dosing system for administering a fluid into or under the skin may have: a micropump having an inlet and an outlet the micropump being configured to transport a fluid from the inlet to the outlet and generate a blocking pressure of at least 20 bar at the outlet; and a nozzle arranged on the outlet side, configured to output the fluid output at the outlet as a free jet so that the fluid of the free jet may be injected into the skin; wherein the micropump has a membrane and a piezo actuator, wherein the micropump has a valve in the form of a passive check valve at the inlet; and wherein the micropump has a valve in the form of a passive check valve at the outlet.

Another embodiment may have a wearable arm strap having a free-jet dosing system as mentioned above.

Still another embodiment may have a patch having a free-jet dosing system as mentioned above.

Embodiments of the present invention provide a free-jet dosing system for applying a fluid (for example medication) under the skin. The free-jet dosing system comprises a (electrically actuateable) micropump having an inlet and an outlet, and a nozzle arranged on the outlet side. The micropump is configured to transport a fluid from the inlet to the outlet and generate a blocking pressure or stall pressure of at least 20 or 25 bar at the outlet. The nozzle is configured to output the fluid output at the outlet at a corresponding pressure (for example 5.0 bar or 9.5 bar) as a free jet, so that the fluid of the free jet is injectable into or under the skin.

The central idea of the present invention is that very small free-jet dosing systems for high pressures (cf. blocking pressure) of up to 40 bar, comprising a dosing chip size of only 7×7×1×mm³, may, for example, be realized by a clever micropump design (for example membrane or diaphragm pump comprising a disproportionately thick membrane or diaphragm and reinforced outlet valve). A precise, low-pain, needleless and subcutaneous application of medication, for example insulin, to the patient or into the skin becomes possible using such free-jet dosing systems.

Depending on the specific drive parameters, the micropump or high-pressure micro membrane pump may be adjusted such that, with each pump stroke, a stroke volume of the micropump is shot through the upper layers of the skin in a jet at a precisely adjustable pressure (for example 20 bar). Due to the small nozzle opening (for example 50 µm to 100 µm) and the defined penetration depth, this injection is painless.

Due to its ultra-compact structure, such a dosing chip may be integrated into watches, patches or teeth. Thus, further embodiments relate to a wearable arm strap or patch having a free-jet dosing system integrated therein. This technology is a considerable breakthrough in particular for diabetes therapy, since it makes pricking by a needle superfluous. Due to the tiny and flat structure, this chip may additionally be integrated into flat patches or wearable devices, like conventional wristwatches, smartwatches or arm straps, for example.

Further embodiments provide a free-jet dosing system comprising a micropump which comprises a membrane and a piezo actuator, wherein the piezo actuator comprises a thickness of at least 150 µm or at least 300 µm or advantageously up to 600 µm or more. Such dosing chips do not only allow the dosing pressure to be adjusted precisely in dependence of which the penetration depth into the skin is determined, but also exhibit low susceptibility to failure, due to its self-sucking ability and high bubble tolerance.

In correspondence with embodiments, the piezo actuator here may be formed by multi-layered ceramics (i.e. by at least two ceramic layers or, advantageously, up to 10, 15 or even 20 ceramic layers). These ceramic layers may optionally be bonded to one another. Such a multi-layered ceramic piezo actuator allows a sufficiently high pressure to be generated in the pump chamber or, in particular, at the outlet thereof with low turn-on voltages (for example 50 volts), but high drive currents. In a micropump of this structure, in corresponding further embodiments, it may also be sensitive to implement the thickness of the membrane to be at least 100 µm or at least 200 µm or, advantageously, even up to 400 µm or even more in order to withstand forces of larger than 20 bar or even up to 40 bar when generating the blocking pressure. A further optional variation for improving the stability of the membrane is biasing same.

Despite the "relatively large" dimensions for the piezo actuator and the membrane, overall dimensions of less than 10×10×2 mm³ may be realized. Structural features for allowing such high blocking pressures relate to (passive) valves (like check valves) both on the inlet and outlet sides. One-way valves may be used here. In correspondence with embodiments, the one-way valve at the outlet comprises at least a cantilever supported on two sides or a membrane supported on one side.

The high chamber pressure with the, at the same time, small dimensions is also made possible by the fact that a nozzle having a very small fluid opening, for example diameter of less than 100 µm or even less than 50 µm, in combination with a high compression field of at least 0.2 is applied in the pump. These small nozzles cause only minimum damage to the skin and thus allow a nearly painless injection.

In correspondence with additional embodiments, the free-jet dosing system comprises a controller which allows setting a drive profile. The penetration depth may be adjusted precisely by the defined drive profile (in contrast to conventional jet dispensers in accordance with the spring principle). In addition, the pump volume may be adjusted precisely, wherein complete driving of a multiple of the smallest volume unit of, for example, 20 nanoliters is possible here. Using the membrane pumps discussed before, repeat frequencies of up to 200 Hz may be achieved since the membrane pump chip also comprises a pump function.

In correspondence with further embodiments, a silver layer may be provided on the nozzle chip or in the chambers and valves, thereby providing for (long) sterility of the medication.

BRIEF DESCRIPTION OF THE DRAWINGS

Embodiments of the present invention will be discussed referring to the appended drawings, in which:

FIG. 3b shows a schematic structural drawing of a free-jet dosing system in the form of a dosing chip included dosing monitoring in accordance with extended embodiments;

FIG. 5b shows a table illustrating design examples for micropumps.

DETAILED DESCRIPTION OF THE INVENTION

Figure 1:
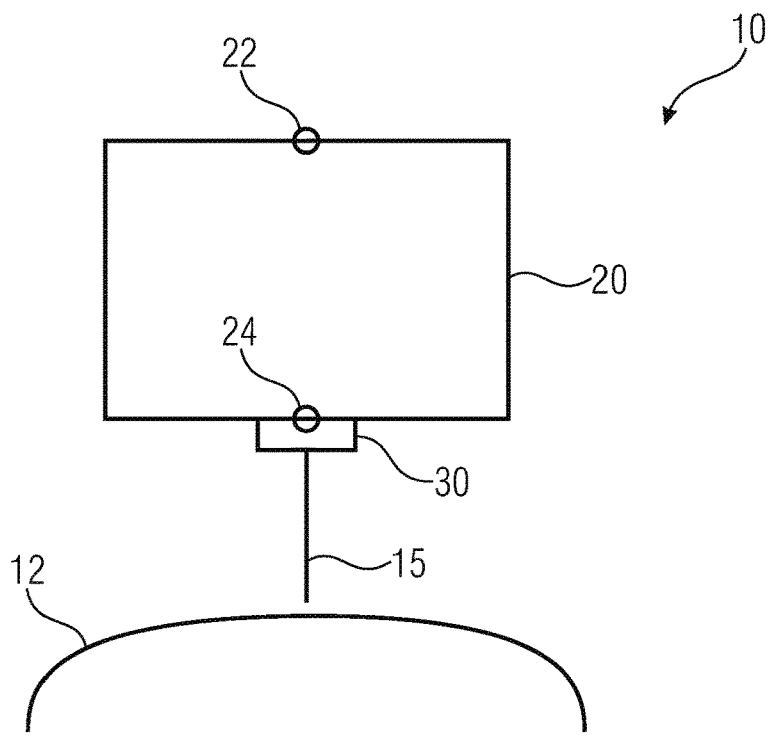
FIG. 1 shows a schematic block diagram of a free-jet dosing system in accordance with a basic embodiment.

Before discussing embodiments of the present invention below referring to figures, it is to be pointed out that equal elements and structures or those of equal effect are provided with equal reference numerals so that the description thereof is mutually applicable or exchangeable.

FIG. 1 shows a free-jet dosing system comprising a micropump 20 and a nozzle 30 arranged on the outlet side. The micropump 20 comprises at least one inlet 22 and one outlet 24, wherein the nozzle 30 is arranged at the outlet 24 or/and coinciding with same. It is also to be pointed out here that the outlet 24 may also have the nozzle 30 integrated therein.

The free-jet dosing system serves for applying a fluid, for example a drug or medication, into or under the skin 12. A free jet 15 is generated at the nozzle 30 by means of the free-jet dosing system 10. For generating the free jet 15, a medication or, generally, the fluid is taken up or sucked in at the inlet 22, transported to the outlet 24 by the pump 20, wherein a so-called blocking pressure of at least 20 bar or even 40 bar is set up. Blocking pressure here means that pressure necessitated for the fluid to flow through the outlet 24. Starting from the high blocking pressure of the fluid, the fluid is then dispensed at a high pressure by means of the nozzle 30, for example more than 10 or 20 bar (or 15 to 30 bar) in the form of the free jet 15 for being injected into the skin 12. For a contactless injection or subcutaneous application, a "sharp" free jet 15 which is generated by the small nozzle 30, for example in the order of magnitude of 50 μm or up to 100 μm, is necessitated apart from the high pressure.

The penetration depth of the free jet 15 (into or under the skin) may be adjusted in dependence on the parameters discussed here. The skin may roughly be subdivided into three layers, covering muscles, tendons and bones. The uppermost layer (30-2000 μm) is the so-called epidermis. The bottom layer is the subcutis (500-30000 μm). The dermis is located therebetween. Injecting into the epidermis or dermis usually does not cause pain since there are no nerves and no blood vessels are damaged. However, the quantities of medication to be introduced in these skin layers are limited so that, with larger quantities, a subcutaneous application or repeated application takes place.

It is to be pointed out here that, in correspondence with embodiments, there is a linear connection between the stroke volume V and the blocking pressure p. The linear connection is caused by the fact that voltage-dependent elements, for example piezo actuators, are used for generating the stroke. The blocking pressure is minimal at a maximum stroke volume $V_0$ (with no back pressure) and maximum ($p_{max}$) at a minimum stroke volume V. The operating point of the micropump 20 (p=20 bar and V=20 nl) is typically arranged in the (linear) region therebetween.

Figure 2:
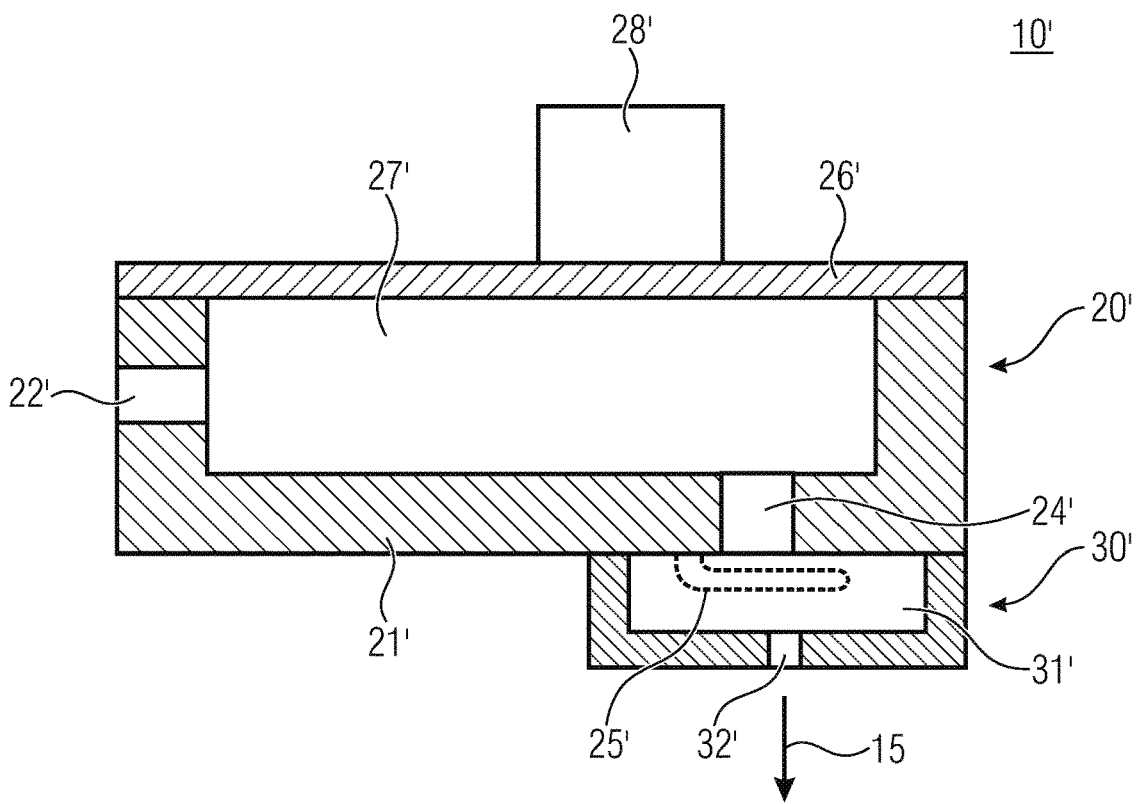
FIG. 2 shows a schematic block diagram of a free-jet dosing system comprising a membrane pump in accordance with another embodiment.

FIG. 2 shows a schematic block diagram of a free-jet dosing system 10', the micropump 20' being implemented as a membrane pump and coupled to a nozzle 30' on the outlet side.

The micropump 20' comprises the casing 21' in which are arranged the inlet 22' and the outlet 24'. In addition, the casing 21' is sealed by the membrane 26' thereby forming a chamber 27' within the pump 20'. The membrane 26' is operated by an actuator 28', for example a piezo actuator.

As a consequence of "actuation" by means of the actuator 28', the volume in the chamber 27' is reduced so that the pressure within increases when filling the chamber 27' with fluid. The pressure increases until reaching the blocking pressure defined by the outlet 24' of, for example, 20 bar. In correspondence with embodiments, the blocking pressure may be defined by an outlet valve 25' which is, for example, realized as a one-way valve. The one-way valve 25' exemplarily includes a valve lid and a spring and is shaped like a cantilever or bending bar arranged on the external side of the casing 21' in an elastic manner, which, in a first pressure state in the chamber 27' (for example <10 bar), seals the outlet 24' and which deforms as a consequence of the pressure within the chamber 27' (>10 bar) so as to release the outlet 24' in dependence on the pressure within the chamber 27'. In this second pressure state, the valve 25' is open so that the fluid may pass from the chamber 27' to the nozzle 30' or into the nozzle chamber 31' to be then output through the nozzle opening 32' in the form of the free jet 15.

For generating a volume pressure around 20 bar (40 bar) within the chamber 27', it is, on the one hand, of advantage for the valve 25' to be implemented correspondingly and, on the other hand, for the pump 20' to be dimensioned correspondingly. Measures for increasing the stability of the valve 25" are, for example, the two-sided support of the bending bar or the usage of corresponding materials. In correspondence with embodiments, the (silicon) casing 21' may be provided with a wall thickness of, for example, greater than 250 μm or 500 μm so as to exhibit sufficient rigidity at the blocking pressures present.

Additionally or alternatively, the drive membrane 26' and the piezo actuator 28' may be designed correspondingly. In correspondence with embodiments, the drive membrane 26' which is, for example, manufactured from silicon may, for example, be implemented to be biased and comprise a thickness of up to 400 μm. In correspondence with further embodiments, the actuator 28' is implemented as a piezo ceramic having a thickness of up to 600 μm. It would also be conceivable here for the piezo actuator 28' to be realized in several layers, i.e., for example, up to 10 or 20 layers.

Figure 3A:
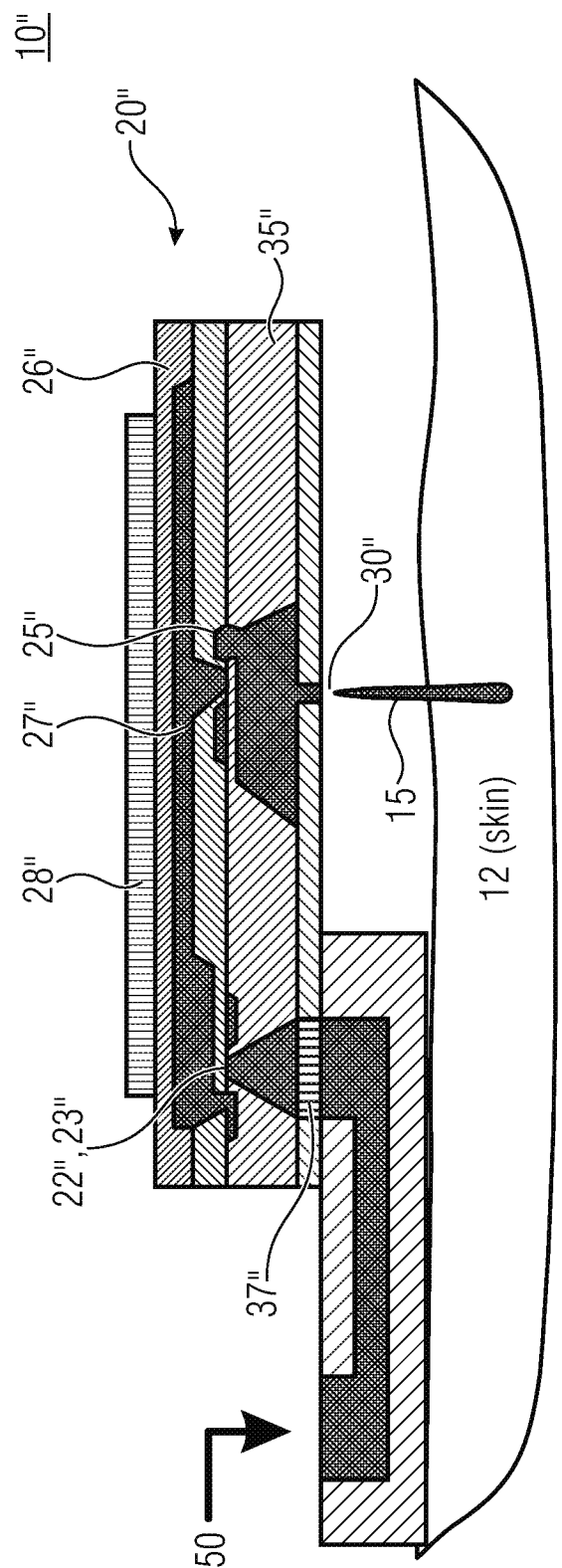
FIG. 3a is a schematic structural drawing of a free-jet dosing system in the form of a dosing chip in accordance with an extended embodiment.

FIG. 3a shows a dosing chip 10" (micro dosing system) comprising a micropump 20" at high a blocking pressure and a free-jet nozzle 30". A so-called nozzle chip 35" is arranged between the micropump 20" and the actual nozzle 30". The micropump 20", nozzle chip 35" and free-jet nozzle 30" together form the so-called basic module. In this embodiment, the basic module is, for example, formed of silicon and forms the actual dosing chip.

Same includes a pump chamber 27" which is limited by a drive membrane 26" and passive check valves 25". A nozzle chip 35" is applied below the valve chip 20", and optionally a particle filter 37" is applied to the inlet 22".

The piezo pump actuator 28" is configured to exhibit a blocking pressure of approximately 40 bar. New ground has been broken as regards the magnitude of the blocking pressure. In addition, a design has been configured for a piezo actuator at 60 bar (FEM simulations and analytical calculations).

Of advantage for such high blocking pressures is increasing the thickness of both the silicon membrane 26" (to up to 400 μm) and the piezo ceramic 28" (to up to 600 μm). In order to reduce the turn-on voltages with very thick ceramics 28", a multi-layered ceramic (with, for example, 10-20 layers) which are provided by a piezo supplier (at present PI Ceramics) in accordance to a specification, may be used. Thus, with a 10-layer multi-layered ceramic with a thickness of 600 μm, the turn-on voltage is only 90 V (instead of 900 V with a monomorphic ceramics), but, due to the higher capacitance of the multi-layer element, the drive electronics (not illustrated) has to provide a drive current greater by a factor of 10. The respective controller has to be configured correspondingly.

Naturally, the high blocking pressure causes smaller a stroke volume. This also reduces the compression ratio (ratio between stroke volume and dead volume) (for example at least 0.2), the bubble tolerance of the dosing chip 10" may suffer. The compression ratio is defined by the ratio between the stroke volume and the dead volume. The stroke volume here is the volume displaced by the membrane at the voltage amplitude with no back pressure. The dead volume is defined as the sum of all the volumes in the pump chamber (with no back pressure) when the membrane is at the lower point of reversal. In order to prevent this, the piezo ceramic is fixed by a bonding process, by biasing the ceramic 28" in a defined manner. Thus, the pump chamber 27" may be reduced to a measure of a few micrometers, thereby reducing the dead volume. This allows making the compression ratio of the dosing chip so great that the dosing chip becomes self-sucking, i.e. configured for sucking fluid from the reservoir 50.

The passive check valves 23" and, in particular, 25" made of silicon are to withstand a pressure pulse of 40 bar. The geometrical dimensions of the valve flap may have to be adapted (for example thicker flap, shorter flap, two-sided support etc.). A nozzle chip 35", also made of silicon, is applied to the lower side of the pump chip 20". Same is advantageously dry-etched by using an SOI wafer. Connecting all the wafers among one another is, for example, done by the silicon fusion bond used, but may also take place by alternative connecting processes, for example eutectic bonding, wafer bonding etc. Alternatively, the dosing chip may also include ceramics or be formed from metal layers, for example spring stainless steel, which are then joined by laser welding or thermal diffusion bonding.

FIG. 3b shows another dosing chip 10''' (for example made of silicon) comprising the micropump 20"(cf. FIG. 3a), the nozzle chip 35''', and a dosing chip 30''' with an integrated nozzle and monitoring functionality. It is to be pointed out here that the actual nozzle has the reference numeral 32".

A suitable dosing chip 35''' and 30''' may be used instead of the nozzle chip. It includes, for example, a piezo resistive pressure sensor (the measuring range of which is configured for a pressure of, for example 40 bar) in the membrane center of which a nozzle is etched (for example by a dry-etching step). The nozzle 32''' serves as a diaphragm flow restriction for pressure reduction and as a nozzle for forming the free jet 15 at the same time.

The pressure sensor may be realized as a Wheatstone bridge. Four resistors, in particular piezo resistive resistors, arranged in a Wheatstone bridge circuit are, for example, provided on the membrane which comprises the nozzle. Deformations of the (piezo resistive) resistors and, thus, of the membrane are measured by means of the Wheatstone bridge circuit using detuning thereof, starting from which the flow rate through the nozzle (flow resistance with defined resistance to flow) may be determined, when knowing the nozzle diameter.

This allows online-monitoring of the mode of functioning of the ejection process: Failure condition caused by gas bubbles: When, for example, there is an air bubble in the pump chamber 27", the pressure necessitated for ejection can no longer be set up, the pressure achievable will form only in accordance with the compression ratio defined by the size of the air bubble.

Another failure condition is when an air bubble is located not in the pump chamber, but in the space between the outlet valve 25" and the nozzle 32'''. In this case, too, the pressure achievable is reduced since the air bubble as a fluidic capacitance buffers the volume stroke.

Both failure conditions result in the free-jet pressure at the nozzle 32''' to be too small so that the medication can no longer penetrate into the skin 12.

The dosing chip measures the reduction in pressure at the nozzle directly and reliably recognizes these failure conditions.

Furthermore, the dosing chip 10''' is also able to recognize a degradation of the micropump 20" (for example a reduction in the drive membrane or also degradation of the microvalves), since both events result in a reduction in the free-jet pressure at the nozzle 32'''.

A short overview of fluid dynamics results achievable by means of the dosing chips 10, 10', 10" and 10''' described above will follow. Characterizing the jet is done using DI water using a stroboscope. The pressure p in front of the nozzle may be derived from the jet speed v, using the following equation: $v=\sqrt{2p/\rho}$, $\rho$ being the density of the liquid (the surface energy for forming the free surface of the jet 15 ("free-jet limit") has been neglected here since it does no longer play a role with high pressures). Alternatively, jetting against a force sensor may take place and the pressure in front of the nozzle be derived using the area. By optimizing the drive parameter of the piezo ceramic, the pressures necessitated for pressing the medication into the skin of approximately 20-30 bar are to be adjusted, depending on the penetration depth of the jet.

Figure 5A:
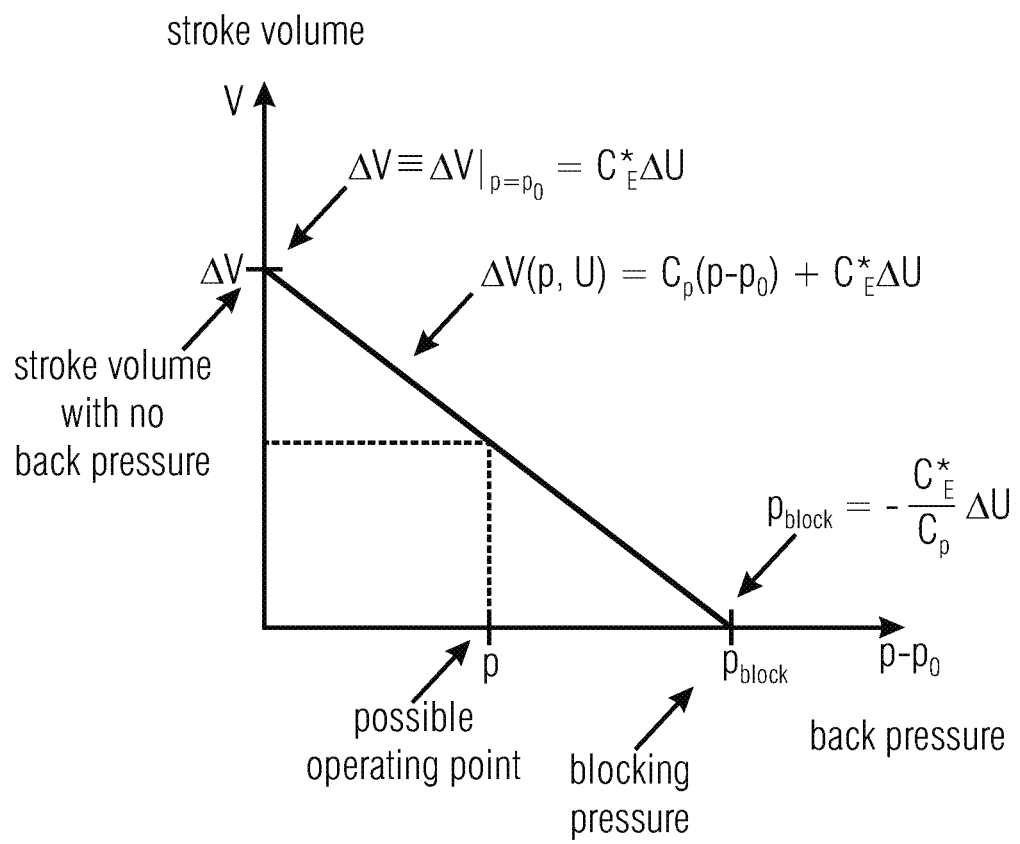
FIG. 5a shows a schematic diagram illustrating the dependence between stroke volume and back pressure for the membrane in micropumps.

The membrane or diaphragm dimensioning may vary in dependence on the purpose of usage and the membrane or chamber volume, as will be explained below. The bellow discussion is made with respect to FIG. 5a and FIG. 5b:

FIG. 5a shows diagram in which the stroke volume $\Delta V$ is plotted over the pump chamber pressure p. Based on the (e.g. linear) function shown by FIG. 5a the operation point can be determined. The mathematical background will be discussed in the following:

Stroke volume $\Delta V$ and fluidic capacitance Cp of piezo actuator: The stroke volume $\Delta V$ of a piezo actuator diaphragm with a pump chamber pressure p and an actuation voltage U can be expressed by:

$$\Delta V(p,U) = C_p(p-p_0) + C^*_E \Delta U$$

$\Delta V$: stroke volume
p: pump chamber pressure
p0: atmosphere pressure
$\Delta U$: voltage stroke
Cp: fluidic capacitance of the actuation diaphragm
CE*: coefficient The coefficients Cp and CE* can be derived by theory. This has been calculated for a circular geometry. Cp depends on:

Yd: Young modulus of the diaphragm
Rd: radius of the diaphragm
Yp: Young modulus of the piezo
Rp: radius of the piezo
v: Poisson number The fluidic capacitance $C_p$ of the actuation diaphragm is defining the volume change of the diaphragm, if the pump chamber pressure changes, it is inversely proportional to the stiffness of the diaphragm.

CE* depends on the same parameters, and additionally on the d31 piezo coefficient. The stroke volume $\Delta V$ will be considered as the stroke volume without back pressure $(p=p_0)$:

$$\Delta V \equiv \Delta V|_{p=p_0} = C^*_E \Delta U$$

The relative maximum pressure head $p_{block}$ can be calculated with $\Delta V=0$:

$$Pblock = -\frac{C^*_E}{C_P}\Delta U$$

The design, especially the design of the diaphragm/pump chamber can be calculated based on above described functions. FIG. 5b shows exemplary four difference design variants using a table. The table includes values for the geometry parameter, e.g. membrane radius, and other operation parameters, like the operation voltages.

Further series of tests will follow, by the dosing chip dosing onto microgram scales. The maximum repeat frequency of jet generation, long-term stability of the dosing quantity and bubble tolerance of the dosing chip, by specifically sucking bubbles, are of great interest. The penetration depth of the jet into a tissue equivalent (for example polyacrylamide gel) is examined in the end. Voltage amplitudes, but also voltage edges (both when setting up and breaking down in a defined manner the jet for avoiding satellite drops) are important optimization parameters. These data then serve as a starting point for product developments, in cooperation with industrial partners and medical partners.

In other words, a needleless compact medication jetter able to apply medication in a painless manner is provided by the free-jet dosing system explained above, thereby obviating pricking by a needle. The dosing unit is so small that it can be integrated in a patch or wristwatch. As has been discussed above, the maximum quantity per injection is limited in particular when injecting into the upper layers of the skin. When, however, the free-jet dosing system is permanently worn at the body, injection may be repeated as frequently as desired (distributing dosing over time), so that, despite the small quantity per individual injection, a sufficient quantity of the medication can be applied, injection into the upper layers of the skin being painless (cf. above).

Figure 4A:
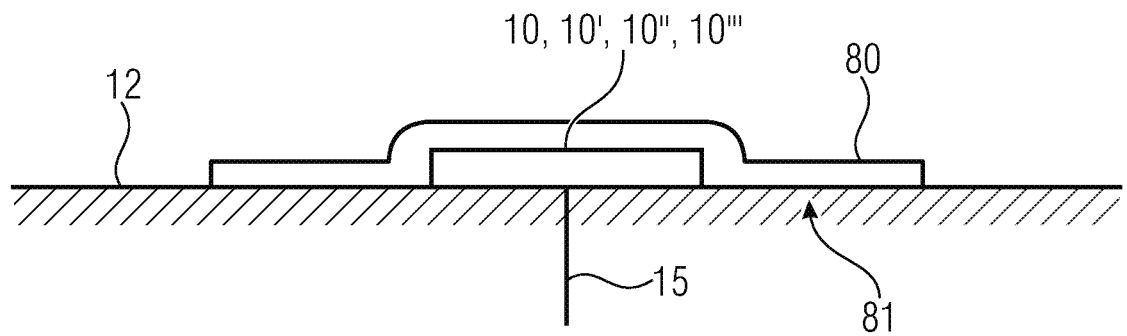
FIG. 4a shows a schematic illustration of a patch comprising a free-jet dosing system.

FIG. 4a shows another embodiment, i.e. a patch 80 having a free-jet dosing system 10, 10', 10" or 10''' integrated into the patch or applied thereto.

As may be recognized, the free-jet dosing system 10, 10', 10", 10''' is arranged instead of the cotton pad typically present in a patch, however different assemblies, for example within the cotton pad, are also conceivable. This arrangement on the sticky side (cf. reference numeral 81) ensures, when the patch is placed on the skin 12, that the free jet 15 impinges thereon, thereby injecting the medication or fluid.

Figure 4B:
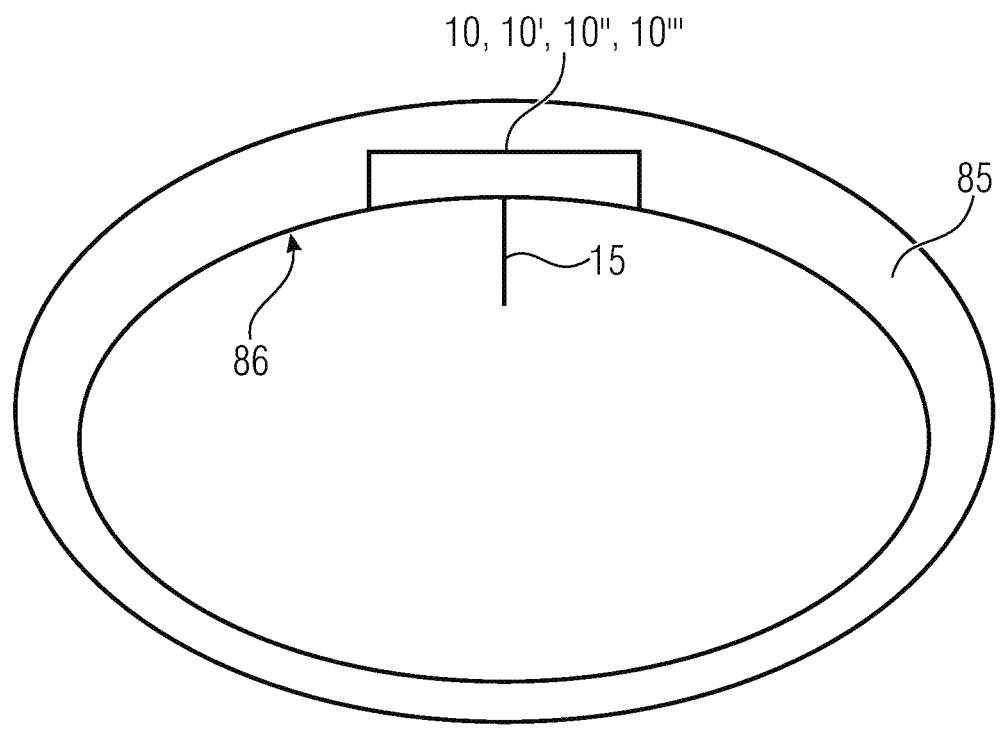
FIG. 4b shows a schematic illustration of an arm strap comprising a free-jet dosing system.

FIG. 4b shows a further wearable variation, namely an arm strap or wristwatch 85, wherein the free-jet dosing system 10, 10', 10" or 10''' is integrated into the arm strap or wristwatch on the inner side (cf. reference numeral 86).

Even when, in the embodiments of FIGS. 4a and 4b, it has not been mentioned explicitly, it is obvious for a person skilled in the art that a corresponding reservoir for the medicine, for example insulin, is provided in the patch 80 or the arm strap 85.

In correspondence with further embodiments, free-jet dosing systems as mentioned above may also include additional drive logics, for example an ASIC, which administers dosing correspondingly or drives the actuators correspondingly so that a corresponding dosage can be administered. Here, the controller will then control the dosing quantity and frequency. The controller may be connected to an external apparatus, for example the smartphone, which is particularly suitable for the embodiments of FIGS. 4a and 4b.

Referring to the embodiment of FIG. 4b comprising the arm strap 85, it is to be mentioned that this arm strap may comprise further elements, for example sensors monitoring the patent.

Even when above embodiments have been discussed in particular in connection with micro dosing pumps in the form of membrane pumps, it is to be pointed out that there are different pumping technologies which may also be employed in the above embodiments or, in particular, in the above embodiment of FIGS. 4a and 4b. The so-called patch pumps or pen technologies are examples of this. These also allow high frequencies of 1 Hz to 200 Hz, wherein these fundamental frequencies are frequently achieved by using microvalves.

Even when, in the above embodiments, the actuator has been discussed in particular as a piezo actuator, it is pointed out that other principles, for example a magnetic actuator, may also be used.

It is common to all the embodiments discussed above that the micro dosing systems comprise very small dimensions of less than $10 \times 10 \times 2$ mm$^3$ or even smaller than $7 \times 7 \times 1$ mm$^3$, wherein further elements, for example reservoir and battery, are to be integrated therein in addition to the actual micro dosing system.

In the above embodiments, it has been assumed that same serve only for administering medication, for example for diabetes patients. Actually, embodiments of the invention are not restricted to such applications. Further examples are local anesthetics (dental medicine or dermatologist), cosmetic medicine (Botox or hyaluronic acid), mass vaccination in the case of epidemics, veterinary medicine, marking animals (instead of brands) or even usage as a novel tool for tattooing.

While this invention has been described in terms of several embodiments, there are alterations, permutations, and equivalents which will be apparent to others skilled in the art and which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

LITERATURE

[1] Samir Mitragotri, Recent Developments in Needle-Free Drug Delivery, The Bridge (USPS 551-240) published the National Academy of Engineering, Val. 38, No. 4, Winter 2008

[2] Trans-Endoscopic Microinjection for Flexible Endoscopy, K. Mutschler, W. Kunert, R. Ingenpaß, K. E. Grund, L. Tanguy, A. Ernst, R. Zengerle, P. Koltay, Biomedical Engineering/Biomedizinische Technik. ISSN (Online) 1862-278X, ISSN (Print) 0013-5585, DOI: 10.1515/bmt-2012-4141, August 2012

[3] http://www.injex.de/, accessed on 22 April 14

[4] http://www.diabetes-deutschland.de/archiv/archiv 2847.html, Prof. Dr. W. A. Scherbaum; Deutsches Diabetes-Forschungsinstitut Düsseldorf, accessed on 22 Apr. 14

[5] Brian D. Hemond, Dawn M. Wendell, N. Cathy Hogan, Andrew J. Taberner, Prof. Ian W. Hunter, a Lorentz-Force Actuated Autoloading Needle-free Injector, Proceedings of the 28th IEEE EMBS Annual International Conference, New York City, U.S.A, Aug. 30-Sep. 3, 2006

[6] S. Weinzierl, Konzept zur Branchenanalyse zur Kommerzialisierung einer piezoelektrisch angetriebenen Mikropumpe für das lndikationsgebiet Diabetes mellitus, master thesis, Georg Siemon-Ohm Hochschule Nürnberg, Fakultät für Betriebswirtschaft, 31 Aur. 2013, realized for Fraunhofer EMFT.

[7] http://www.industryreportstore.com/insulin-delivery-devices-market-to-2019-simplified-pump-solutions-and-low-cost-pens-represent-distinct-regional-growth-drivers.html; accessed on 29 Apr. 2014

[8] M. Wackerle, A. Drost, M. Richter: A novel device for high frequency ejection of nanoliter jets, proceedings Actuator 2002, 8th International Conference on New Actuators, 10-12 Jun. 2002, Bremen, Germany, pp. 227-230

The invention claimed is:

1. A free-jet dosing system for administering a fluid into or under the skin, comprising: a micropump comprising an inlet and an outlet the micropump being configured to transport the fluid from the inlet to the outlet and generate a blocking pressure of at least 20 bar at the outlet; and a nozzle arranged on a side of the outlet, configured to output the fluid at the outlet as a free jet such that the fluid of the free jet is injected into the skin; wherein the micropump comprises a membrane and a piezo actuator, wherein the micropump comprises a valve in the form of a passive check valve at the inlet; and wherein the micropump comprises a valve in the form of a passive check valve at the outlet; wherein the piezo actuator comprises a thickness between 150 µm to 600 µm; and wherein the membrane comprises a thickness between 100 µm to 400 µm and wherein the membrane is biased.

2. The free-jet dosing system in accordance with claim 1, wherein the micropump is coupled to drive electronics or an ASIC for driving.

3. The free-jet dosing system in accordance with claim 1, wherein the passive check valve at the inlet is a one-way valve.

4. The free-jet dosing system in accordance with claim 1, wherein the micropump comprises a compression ratio of 0.2.

5. The free-jet dosing system in accordance with claim 1, wherein the nozzle comprises a fluid opening diameter between 50 µm to 100 µm.

6. The free-jet dosing system in accordance with claim 1, wherein the free-jet dosing system comprises a maximum external dimension of 10×10×2 mm.

7. The free-jet dosing system in accordance with claim 1, comprising a pressure sensor which is coupled to the nozzle on an output side and configured to determine a drop in pressure and/or flow rate of the fluid.

8. The free-jet dosing system in accordance with claim 1, wherein the micropump and/or the nozzle comprise(s) a silver coating and/or another antibacterial coating.

9. The free-jet dosing system in accordance with claim 1, wherein the free-jet dosing system comprises a fluid reservoir which is arranged on an input side.

10. The free-jet dosing system in accordance with claim 1, wherein the piezo actuator comprises a multi-layered ceramic comprising at least 2, 10 or 20 ceramic layers and/or wherein the ceramic layers are bonded to one another.

11. The free-jet dosing system in accordance with claim 10, wherein the free-jet dosing system comprises drive electronics for controlling the micropump, and wherein the drive electronics are configured to provide the piezo actuator with energy with a voltage between 50 V to 200V.

12. The free-jet dosing system in accordance with claim 1, wherein the passive check valve at the outlet is a one-way valve.

13. The free-jet dosing system in accordance with claim 12, wherein the passive check valve arranged at the outlet comprises a cantilever supported on two sides or a membrane valve supported on all sides.

14. A wearable arm strap comprising a free-jet dosing system in accordance with claim 1.

15. A patch comprising a free-jet dosing system in accordance with claim 1.

* * * * *